United States Patent [19]
Kim

[11] Patent Number: 5,864,066
[45] Date of Patent: Jan. 26, 1999

[54] VIBRATION DETECTING SENSOR WITH TEMPERATURE COMPENSATING PIEZOELECTRIC ELEMENT

[75] Inventor: Tae-ho Kim, Kyungki-do, Rep. of Korea

[73] Assignee: Samsung Electronics, Co., Ltd., Rep. of Korea

[21] Appl. No.: 733,931

[22] Filed: Oct. 18, 1996

[30] Foreign Application Priority Data

Feb. 26, 1996 [KR] Rep. of Korea .......................... 96-4694

[51] Int. Cl.[6] ..................................................... G01H 11/08
[52] U.S. Cl. ................................. 73/658; 73/766; 310/315
[58] Field of Search ........................... 73/658, 497, 708, 73/766, DIG. 4, 654; 310/315, 324, 346

[56] References Cited

U.S. PATENT DOCUMENTS

| | | | |
|---|---|---|---|
| 3,877,308 | 4/1975 | Taylor | 374/133 |
| 3,940,974 | 3/1976 | Taylor | 73/DIG. 4 |
| 4,052,979 | 10/1977 | Scherr et al. | |
| 4,531,267 | 7/1985 | Royer | 310/324 |
| 4,705,981 | 11/1987 | Inoue et al. | 310/324 |
| 4,755,975 | 7/1988 | Ito et al. | 310/324 |
| 5,551,437 | 9/1996 | Lotscher | 600/485 |

FOREIGN PATENT DOCUMENTS

| | | |
|---|---|---|
| 0 031 614 A1 | 7/1981 | European Pat. Off. . |
| 0 210 723 A1 | 2/1987 | European Pat. Off. . |
| 0 216 326 A2 | 4/1987 | European Pat. Off. . |
| 0 264 666 A1 | 4/1988 | European Pat. Off. . |
| WO 92/08329 | 5/1992 | WIPO . |
| WO 94/13207 | 6/1994 | WIPO . |

*Primary Examiner*—John E. Chapman
*Attorney, Agent, or Firm*—Burns, Doane, Swecker & Mathis LLP

[57] ABSTRACT

A vibration detecting sensor includes a vibrating plate, a vibration detecting piezo-electric element attached to the upper surface of the vibrating plate, a temperature compensating piezo-electric element attached to the upper surface of a second plate, covering members for covering the respective plates, and lead-in wires connected electrically to the respective piezo-electric elements.

5 Claims, 3 Drawing Sheets

5,864,066

VIBRATION DETECTING SENSOR WITH TEMPERATURE COMPENSATING PIEZOELECTRIC ELEMENT

BACKGROUND OF THE INVENTION

The present invention relates to a vibration detecting sensor using piezo-electric elements, and more particularly to a vibration detecting sensor capable of eliminating the effects of temperature and noise.

Generally, a vibration detecting sensor is used in an electronic sphygmomanometer and also used for detecting vibrations in a machine.

Referring to FIGS. 1 through 3, a conventional vibration detecting sensor is comprised of a circular vibrating plate 1, a covering member 2 covering the circular vibrating plate 1, a piezo-electric element 3 attached to the center of the upper surface of the vibrating plate 1, and a lead-in wire 4 connected electrically to the piezo-electric element 3.

In the conventional vibration detecting sensor, the vibrating plate 1 is composed of a material such as plastics or rubber having metallic particles distributed therein. The piezo-electric element 3 made of a complex material composed of a rubber or a synthetic resin having ferro-electric particles such as PZT or $BaTiO_2$ distributed therein, is attached to the vibration plate 1 by an adhesive. The covering member 2 composed of a metallic material includes a cylindrical wall 2a and a circular ceiling 2b on top of the wall 2a. At the bottom of the wall 2b, there is a channel-shaped section 2c such that the vibrating plate 1 snaps into the channel shaped section 2c and combines with the covering member 2. Also, a slot 2d is formed through the wall 2a and the channel-shaped section 2c so that the lead-in wire 4 can be inserted within the covering member 2. An end of a central wire 4a in the inserted lead-in wire 4 is soldered onto the upper surface of the piezo-electric element 3 by a soldering portion 5, and the shielding wire 4b of the lead-in wire 4 is connected to the wall 2a, also by soldering.

When the vibrating plate 1 of the above-described conventional vibration detecting sensor is placed into contact near an arterial blood vessel of a person or a machine, the vibrating plate 1 vibrates according to the pulses of the person or the vibrations of the machine, and to thereby an electrical potential difference between the upper and lower surface of the piezo-electric element 3. The vibrating plate 1 electrically conducts through the metallic particles distributed therein, and the shielding wire 4b connected to the wall 2a of the covering member 2 is also connected electrically to the bottom side of the piezo-electric element 3. Thus, electrical potential differences generated on the piezo-electric element 3 is output as an electric signal via the lead-in wire 4, and thus vibrations can be detected.

However, because the above-described conventional vibration detecting sensor uses a single-plate piezo-electric element, there are problems in that error signals are generated due to temperature changes of its surroundings. Also, because the lead-in wire 4 is inserted into the covering member 2 through the slot 2d on the slot 2a, external noises can penetrate through the hole 2d.

SUMMARY OF THE INVENTION

With a view to overcome or reduce the above problems, an object of the present invention is to provide a vibration detecting sensor capable of removing the influence of temperature change of the surroundings and preventing external noises, thus improving the vibration detecting efficiency.

To obtain the above object, there is provided a vibration detecting sensor including a vibrating plate, a vibration detecting piezo-electric element attached to the upper surface of the vibrating plate, a temperature compensating piezo-electric element attached to the upper surface of the vibrating plate, a covering member for covering the vibrating plate, and lead-in wires connected electrically to the respective piezo-electric elements.

BRIEF DESCRIPTION OF THE DRAWINGS

The above objects and advantages of the present invention will become more apparent by describing in detail preferred embodiments thereof with reference to the attached drawings in which.

DETAILED DESCRIPTION OF THE INVENTION

Figure 1:
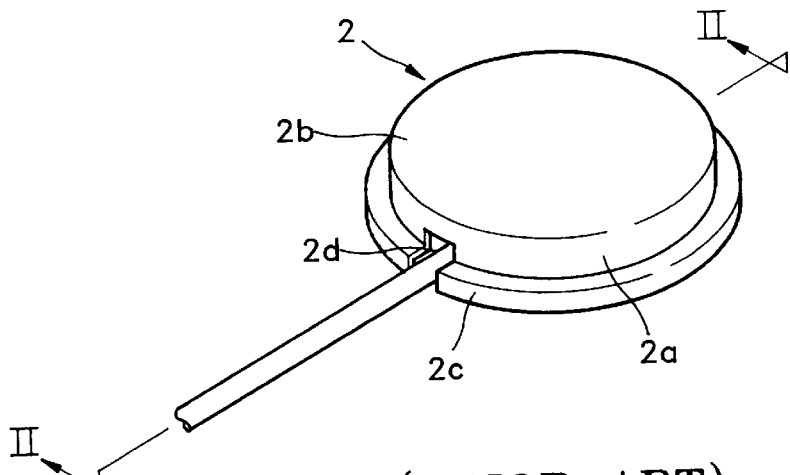
FIG. 1 is a perspective view schematically illustrating a conventional vibration detecting sensor.
Figure 2:
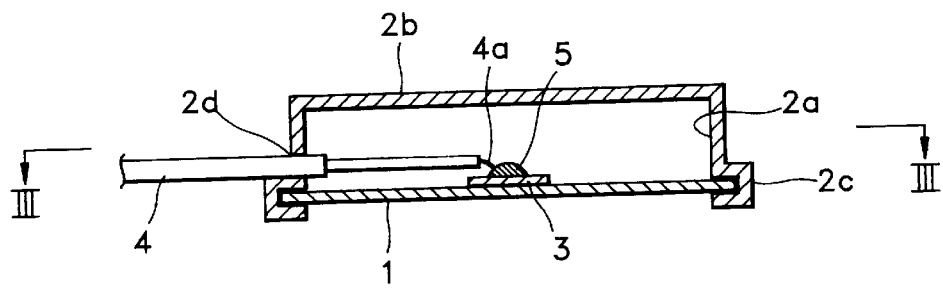
FIG. 2 is a sectional view of the sensor in FIG. 1 cut along the line II—II.
Figure 3:
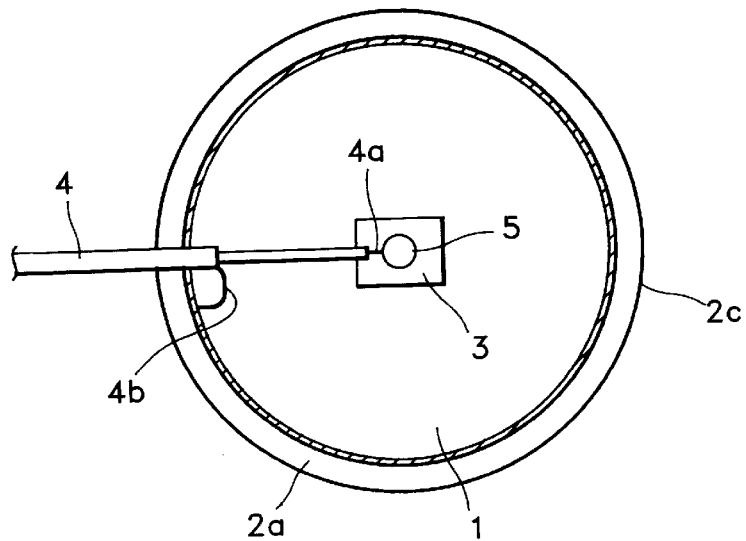
FIG. 3 is a sectional view of the sensor taken along the line III in FIG. 2.
Figure 4:
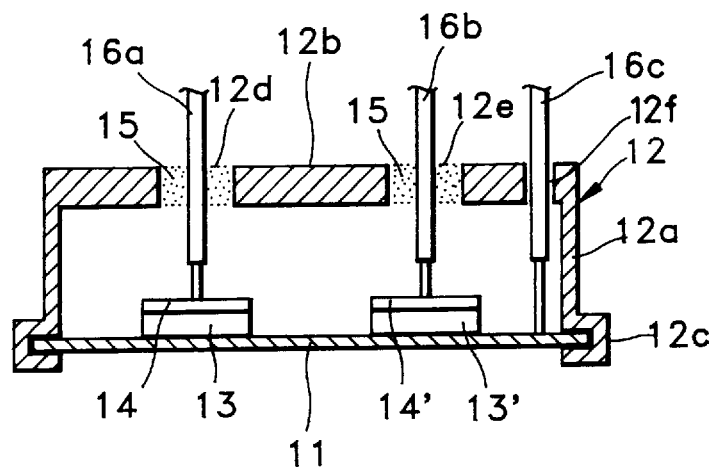
FIG. 4 is a sectional view schematically illustrating a vibration detecting sensor according to an embodiment of the present invention.

Referring to FIG. 4, a vibration detecting sensor according to a first embodiment of the present invention is comprised of a circular vibrating plate 11, a covering member 12 covering the vibrating plate 11, a vibration detecting piezo-electric element 13 attached to the upper surface of the vibrating plate 11, a temperature compensating piezo-electric element 13' attached parallel to the vibration detecting piezo-electric element 13 on the upper surface of the vibrating plate 11, and lead-in wires 16a and 16b connected electrically to the piezo-electric elements 13 and 13', respectively.

In the above structure, the vibrating plate 11 is composed of a material such as plastics or rubber having metallic particles distributed therein. The piezo-electric elements 13 and 13' made of complex substrates each of which is composed of an elastic material such as a synthetic resin or rubber having ferro-electric particles such as PZT or $BaTiO_2$ distributed therein, are attached to the upper side of the vibrating plate 11 by an adhesive. The covering member 12 composed of a metallic material includes a cylindrical wall 12a and a circular ceiling 12b on top of the wall 12a. At the bottom of the wall 12b, there is a channel-shaped section 12c such that the vibrating plate 11 snaps into the channel-shaped section 12c and combines with the covering member 12. Also, holes 12d, 12e and 12f are formed through the ceiling 12b so that the lead-in wires 16a and 16b and shielding wire 16c can be respectively inserted into the covering member 12. Moreover, the holes 12d and 12e are sealed with a glass material 15. The wire ends (not shown) of the lead-in wires 16a and 16b inserted through the holes 12d and 12e are respectively soldered onto the upper surfaces of the piezo-electric elements 13 and 13', and the shielding wire 16c for ground is connected to the vibrating plate 11.

It is preferable that in the above-structured vibration detecting sensor, the thickness of the vibrating plate 11 is less than that of the piezo-electric elements 13 and 13' to minimize vibration attenuation.

The piezo-electric elements 13 and 13' have silver electrode layers 14 and 14', respectively, on the upper sides thereof. While the polarizing directions of the electrode layers 14 and 14' are identical, the lead-in wires 16a and 16b are connected to input terminals of a difference amplifier 100 (see FIG. 7). By means of such connection, the difference amplifier 100 amplifies the difference (V1–V2) between two input signals V1 and V2, from which a pure vibration signal can be obtained as an output signal.

Therefore, because the vibration detecting sensor according to the first embodiment of the present invention removes error signals due to temperature change of the surroundings by using the temperature compensating piezo-electric element 13', only a pure vibration component is detected and thus the detection reliability of the vibration detector is enhanced. Moreover, because the holes 12d and 12e through which the lead-in wires 16a and 16b are inserted are sealed with the glass material 15, it is possible to prevent external noises from penetrating the covering member 12, contrary to the conventional vibration detecting sensor.

Figure 7:
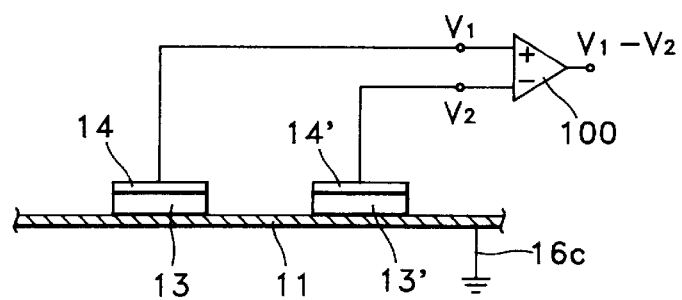
FIG. 7 is a connecting diagram of the output lead-in wires of the vibration detecting sensor according to the above embodiments of the present invention.

The connection diagram showing output lead-in wires in a vibration detecting sensor shown in FIG. 7 can be applied not only to the first embodiment but also to the other embodiments according to the present invention in the same manner.

Figure 5:
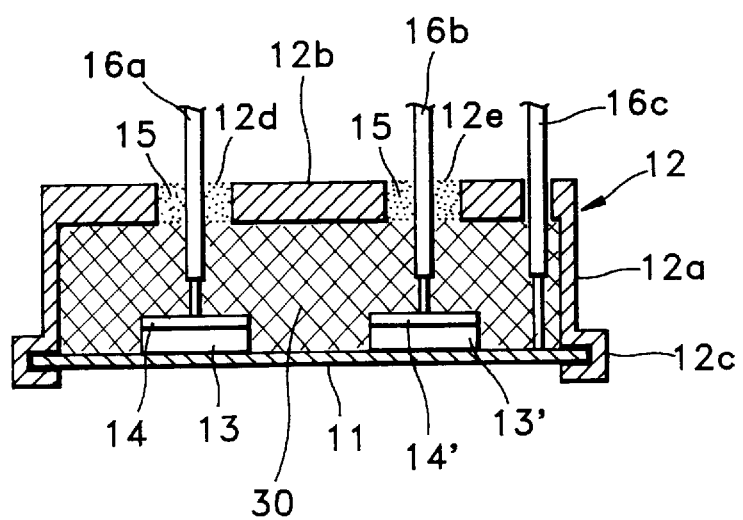
FIG. 5 is a sectional view schematically illustrating a vibration detecting sensor according to another embodiment of the present invention.

A vibration detecting sensor according to a second embodiment of the present invention, shown in FIG. 5, can be characterized in that the space within the covering member 12 is filled with an elastic resin 30. Such constitution is more effective for shielding the piezo-electric elements against noises.

Figure 6:
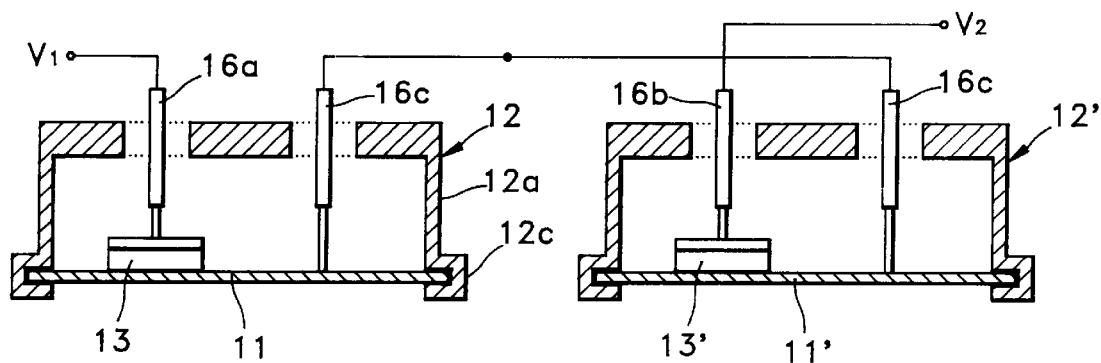
FIG. 6 is a sectional view schematically illustrating a vibration detecting sensor according to still another embodiment of the present invention.

A vibration detecting sensor according to a third embodiment of the present invention, shown in FIG. 6, can be characterized by separate covering member 12 and case member 12' and vibrating plate 11 and a base 11' for the vibration detecting piezo-electric element 13 and the temperature compensating piezo-electric element 13'. Such constitution makes it possible for the temperature compensating piezo-electric element 13' to thoroughly exclude vibration influences, and thus the vibration component due to temperature changes to the surrounding can be removed more effectively.

As described above, a vibration detecting sensor according to embodiments of the present invention can remove the influence of temperature changes to the surrounding and external noises by using a temperature compensating piezo-electric element, and can also enhance vibration detecting efficiency by filling the holes through which the lead-in wires are inserted with a glass material, and filling the inner space of the vibration detecting sensor with an elastic resin.

Such a vibration detecting sensor is not limited to the above-described embodiments but can be modified within the scope of the claims. For example, a vibration detecting sensor according to an embodiment of the present invention can also be effective for detecting low frequency band vibrations due to centrifugal forces in a spin cycle of a washing machine.

What is claimed is:

1. A vibration detecting sensor comprising:

vibration detecting means comprising a vibrating plate;

a vibration detecting piezo-electric element attached to an upper surface of said vibrating plate;

a covering member for covering said vibrating plate;

a lead-in wire connected electrically to said vibration detecting piezo-electric element; and temperature compensating means for removing the influence of temperature change of the surroundings, wherein said temperature compensating means is connected electrically to said vibration detecting means and comprises:

a case member;

a temperature compensating piezo-electric element attached to an inner surface of said case member; and a lead-in wire connected electrically to said temperature compensating piezo-electric element.

2. The vibration detecting sensor as claimed in claim 1, wherein said covering member has holes and said lead-in wires are inserted through said holes, respectively.

3. The vibration detecting sensor as claimed in claim 2, wherein said holes are sealed with a glass material.

4. The vibration detecting sensor as claimed in claim 1, wherein the space between said covering member and said vibrating plate is filled with an elastic resin.

5. The vibration detecting sensor as claimed in claim 1, wherein the thickness of said vibrating plate is less than that of said piezo-electric elements.

* * * * *